(12) United States Patent
Jukarainen et al.

(10) Patent No.: US 6,794,464 B2
(45) Date of Patent: Sep. 21, 2004

(54) MEMBRANE OR MATRIX FOR CONTROLLING THE PERMEATION RATE OF DRUGS

(75) Inventors: Harri Jukarainen, Turku (FI); Tommi Markkula, Turku (FI); Juha Ala-Sorvari, Turku (FI); Matti Lehtinen, deceased, late of Piispanristi (FI), by Pirkko Lehtinen, Legal Representative; Jarkko Ruohonen, Vanhalinna (FI)

(73) Assignee: Schering Oy, Turku (FI)

( * ) Notice: Subject to any disclaimer, the term of this patent is extended or adjusted under 35 U.S.C. 154(b) by 0 days.

(21) Appl. No.: 10/298,195

(22) Filed: Nov. 18, 2002

(65) Prior Publication Data

US 2003/0096920 A1 May 22, 2003

Related U.S. Application Data

(63) Continuation-in-part of application No. 09/701,547, filed as application No. PCT/FI99/00511 on Jun. 11, 1999, now abandoned.

(30) Foreign Application Priority Data

Jun. 30, 1998 (FI) .................................................. 981506

(51) Int. Cl.$^7$ .............................................. C08L 83/10
(52) U.S. Cl. ...................... 525/474; 556/444; 556/445; 568/673; 528/31; 528/15; 528/25; 528/24; 424/482; 424/468; 525/477; 524/492
(58) Field of Search ................................. 556/444, 445; 568/673; 528/31, 15, 24, 25; 424/482, 468; 525/474, 477; 524/492

(56) References Cited

U.S. PATENT DOCUMENTS

| 3,836,560 | A | | 9/1974 | Prokai et al. ......... 260/448.8 R |
| 4,248,750 | A | * | 2/1981 | Murakami et al. |
| 4,600,751 | A | | 7/1986 | Lee et al. .................... 525/404 |
| 5,412,004 | A | * | 5/1995 | Tachibana et al. |
| 5,889,108 | A | | 3/1999 | Zhang ........................ 524/862 |
| 6,013,711 | A | | 1/2000 | Lewis et al. ................ 524/265 |
| 6,476,079 | B1 | | 11/2002 | Jukarainen et al. ...... 514/772.4 |
| 2003/0096921 | A1 | | 5/2003 | Jukarainen et al. ......... 525/474 |

FOREIGN PATENT DOCUMENTS

| EP | 545 002 | 6/1993 |
| EP | 882 753 | 12/1998 |
| FI | 973 427 | 2/1999 |

OTHER PUBLICATIONS

Polymer Handbook, $2^{nd}$ Ed., Wiley–Intersicience, 1975, p. III–157.*
Hans W. Haesslin, et al., "Dimethylsiloxane–ethylene oxide block copolymers, 1, Microphase separation of low segment mass copolymers and their compatibility with water and oil", 185 *Makromol. Chem.* 2625–2645 (1984).
Hans W. Haesslin, "Dimethylsiloxane–ethylene oxide block copolymers 2, Preliminary results on dilute solution properties", 186 *Makromol. Chem.* 357–366 (1985).
Katherine L. Ullman et al, "Drug Permeability of Modified Silicone Polymers I. Silicone–organic Block Copolymers", 10 *J. Controlled Release* 251–260 (1989).
Chemical Abstracts 126: 2000090, "Synthesis and Drug Release Property of Polysiloxane Containing Pendant Long Alkyl Ether Group" (1997).
Meals et al., *Silicones* 115–116 (1959).
*Sun et al., "Effect of Polymer Composition on Steroid Permeation: Membrane Permeation Kinetics of Androgens and Progestins," 5 *J. Controlled Release* 69–78 (1987).

* cited by examiner

*Primary Examiner*—Kuo-Liang Peng
(74) *Attorney, Agent, or Firm*—James C. Lydon

(57) ABSTRACT

A membrane or matrix for controlling the permeation rate of a drug, where the membrane or matrix includes a siloxane-based elastomer composition which contains at least one elastomer and optionally a non-crosslinked polymer. The elastomer composition includes poly(alkylene oxide) groups, and the poly(alkylene oxide) groups are present as blocks in a chain of the elastomer or the polymer, or as blocks and alkoxy-terminated grafts of polysiloxane units, the blocks or blocks and grafts being linked to the polysiloxane units by silicon-carbon bonds, with at least three blocks being present in the elastomer or polymer chain. Methods for the preparation of the elastomer composition are also disclosed.

20 Claims, No Drawings

MEMBRANE OR MATRIX FOR CONTROLLING THE PERMEATION RATE OF DRUGS

This application is a continuation-in-part of application Ser. No. 09/701,547, filed Nov. 30, 2000, Now abandoned which is a U.S. National Stage of International application PCT/FI99/00511, filed Jun. 11, 1999 and published on Jan. 6, 2000 in the English Language.

The invention relates to a membrane or matrix intended for controlling the permeation rate of a drug, wherein said membrane or matrix comprises a siloxane-based elastomer composition, and to a method for the preparation of said elastomer composition.

STATE OF THE ART

Polysiloxanes, in particular poly(dimethyl siloxane) (PDMS), are highly suitable for use as a membrane or matrix regulating the permeation rate of drugs in various drug forms, in particular in implants and IU systems. Polysiloxanes are physiologically inert, and a wide group of drugs are capable of penetrating polysiloxane membranes, which also have the required strength properties.

It is known from the literature that the adding of poly(ethylene oxide) groups, i.e. PEO groups, to a PDMS polymer may increase the permeation rate of drugs. Publication KL Ullman et al., Journal of Controlled Release 10 (1989) 251–260, describes membranes prepared from a block copolymer which contains PEO and PDMS and the penetration of various steroids through these membranes. It is noted in the publication that an increasing PEO amount in the block polymer tends to increase the penetration of hydrophilic steroids, while the penetration of lipophilic steroids decreases. The block copolymer described in the publication is very complicated in its structure and preparation, and would therefore not be facile in more extensive technical production. Furthermore, said copolymer and thus prepared membrane contains urea groups as well as hydrolyzable urethane groups, of which are undesirable in long-term medical applications as a possible site for degradation or reaction. The process for manufacturing said copolymer, which is also described in U.S. Pat. No. 4,600,751 (see below) uses compounds such as isocyanates, which are toxic and undesirables for environmental and health reasons.

U.S. Pat. No. 4,600,751 discloses an elastomer that cannot be made into a matrix or membrane. According to Tables 1 and 2 of the cited document, when the elastomer composition contains no monomer (Examples 1 and 2, MMA content is 0%), the physical properties of its elastomer are insufficient for such use, indicating in fact that the product obtained in Examples 1 and 2 is not an elastomer. In Table 2, it is shown that it has not been possible to measure for example the tensile strength of the elastomer. The best properties in this respect are achieved when there is 40% of MMA (leading to an elongation at break of 140%), whereas with the elastomers according to the present invention, it is possible to achieve elongations at break in order of 3500 to 4600% at 109 Mpa. Thus, the method in this reference requires the use of additional monomer to crosslink the polymer to form an elastomer. There is no indication that it would be possible to achieve the process according to the present invention by omitting the monomer.

The article "Effect of polymer composition on steroid permeation: membrane permeation kinetics of androgens and progestins" by Sun et al., Journal of Controlled Release, 5 (1987) 69–78, is partly by the same authors as the publication and patent mentioned above. In this document, it is stated that the permeation rate for steroids was higher with PDMS than with PDMS/PEO/PMMA copolymer. It is also stated that the incorporation of PMMA drastically decreases the rate of steroid permeation due to the presence of less permeable "hard" PMMA domains. Thus, the elastomer described in U.S. Pat. No. 4,600,751 that is crosslinked in the presence of a monomer (styrene, methyl acrylate and methyl (meth)acrylate being given as examples, contains such less permeable domains of for example PMMA. Therefore, in a system as described in U.S. Pat. No. 4,600,751 where monomers are used, said monomers react also with each other thus forming micelles that have a glass transition temperature that is above the body temperature, i.e. above 37° C. Typically these polymers have a glass transition temperature that is well above 100° C., thus making these polymers rigid at body temperature. This in consequence decreases the permeation rates of active agents.

U.S. Pat. No. 6,013,711 discloses grafted elastomers as well as one two-block elastomer. However, an elastomer comprising both blocks and grafts is not disclosed. These siloxane-polyether copolymers are prepared according to U.S. Pat. No. 6,103,847. The process taught by this patent cannot be used to prepare the multiblock elastomers of the present invention, or for preparing the block-graft-elastomers according to the invention, since the sole examples of polymers having poly(alkylene oxide) blocks are hydroxy-terminated, and thus cannot be crosslinked according to the present invention. The document also fails to disclose crosslinking with peroxide.

OBJECT OF THE INVENTION

The object of the invention is to provide an elastomer composition which is easy to prepare, through which a drug migrates at the desired rate, and which gives the membrane the required mechanical properties.

The object of the invention is in particular to provide an elastomer composition through which the permeation rate of drugs with hormonal action can be controlled.

SUMMARY OF THE INVENTION

The invention thus relates to a membrane or matrix for controlling the permeation rate of a drug, the membrane or matrix comprising a siloxane elastomer composition comprising at least one elastomer and optionally a non-crosslinked polymer, wherein the elastomer composition comprises poly(alkylene oxide) groups and the poly(alkylene oxide) groups are present as blocks in a chain of the elastomer or non-crosslinked polymer, or as blocks and alkoxy-terminated grafts of polysiloxane groups, said blocks or blocks and grafts being linked to the polysiloxane groups by silicon-carbon bonds and said elastomer compositions glass transition temperature is less than 35° C., with the proviso that there are at least three blocks in the elastomer composition.

The invention also relates to a method for the preparation of a siloxane elastomer, including a) crosslinking a vinyl-functional polymer component and a hydride-functional siloxane component in the presence of a catalyst and in the absence of monomer, or
b) crosslinking a polymer component in the presence of a peroxide catalyst and in the absence of monomer, wherein (alkylene oxide) groups are present in the elastomer or polymer as blocks in a chain of said elastomer or polymer, or as blocks and alkoxy-terminated grafts of polysiloxane groups, said blocks or blocks and grafts being linked to polysiloxane groups in said chain by silicon-carbon bonds, there being at least three blocks in said elastomer composition.

DETAILED DESCRIPTION OF THE INVENTION

General Description of the Elastomer Composition

The term "elastomer composition" may stand for one single elastomer, in which case the polysiloxane groups which contain poly(alkylene oxide) groups are present in the said elastomer.

The glass transition temperature of the elastomer composition according to the present invention is less than 35° C.

According to another embodiment, the elastomer composition may be made up of two elastomers which are interlaced, one inside the other. In this case the first elastomer comprises poly(alkylene oxide) groups and the poly (alkylene oxide) groups are present in the elastomer as blocks, or as blocks and alkoxy-terminated grafts of polysiloxane groups, the said blocks or blocks and grafts being linked to the polysiloxane groups by silicon-carbon bonds, or as a mixture of these forms, and wherein the second elastomer comprises a siloxane elastomer, suitably a poly (dimethyl siloxane)-based elastomer. The said second elastomer may optionally also include poly(alkylene oxide) groups. These poly(alkylene oxide) groups may also be present either as blocks or as blocks and alkoxy-terminated grafts of poly(dimethyl siloxane) groups, the said blocks or blocks and grafts being linked to the poly(dimethyl siloxane) groups by silicon-carbon bonds. The poly(alkylene oxides) may also in this elastomer be present as a blend of the options mentioned above.

According to a third embodiment, the elastomer composition may be a blend which includes a siloxane-based elastomer, which is, for example, made up of PDMS, and at least one straight-chain polysiloxane copolymer which includes poly(alkylene oxide) groups. In this case the poly (alkylene oxide) groups are present in the said polymer either as blocks, or as blocks and alkoxy-terminated grafts of polysiloxane groups, these blocks or blocks and grafts being linked to the polysiloxane groups by silicon-carbon bonds. The poly(alkylene oxide) groups may, of course, also be present in the polymer as a blend of the forms mentioned. In this embodiment, the siloxane-based elastomer may also contain poly(alkylene oxide) groups, in which case these poly(alkylene oxide) groups are present in the elastomer either as blocks or as blocks and alkoxy-terminated grafts of polysiloxane groups, these blocks or grafts being linked to the polysiloxane groups by silicon-carbon bonds. The poly (alkylene oxide) groups may also be present as a blend of the forms mentioned.

Of course, the elastomer composition may also be made up of two elastomers interlaced one inside the other, as above, and at least one straight-chain polysiloxane copolymer which includes poly(alkylene oxide) groups.

As summarized above, there are at least three blocks of poly(alkylene oxide) groups present in the elastomer composition. The three block requirement is important to mechanical properties such as tensile strength and elongation. The inventors have discovered that when the length of the block polymer is increased, the mechanical properties of an elastomer prepared from the block polymer are improved.

The poly(alkylene oxide) groups of the elastomer composition may suitably be, for example, poly(ethylene oxide) groups (PEO groups).

The polysiloxane units of the elastomer composition are preferably groups having the formula $$—(SiR'R''O)_q SiR'R''—$$

where R' and R'' are selected from the group consisting of
a) free groups which are the same or different and which are a lower alkyl group or a phenyl group in which case said alkyl or phenyl group may be substituted or unsubstituted, or alkoxy-terminated poly(alkylene oxide) groups having the formula —$R^3$—O—(CHRCH$_2$O)$_m$-alk, where alk is a lower alkyl group, R is hydrogen or lower alkyl, $R^3$ is a linear or branched $C_2$–$C_6$ alkylene and m is 1 to 30,
b) bonds formed from the hydrogen or alkenyl groups to other polymer chains in the elastomer, and as alkoxy-terminated grafts of polysiloxane groups or as blocks or as a mixture of said grafts and said blocks, the said grafts or blocks being linked to the polysiloxane groups by silicon-carbon bonds,
c) optionally unreacted groups selected from the group consisting of hydrogen, vinyl and vinyl-terminated alkene, and q is 1 to 3000.

The term "lower alkyl" stands here and generally in the description of the present invention for $C_1$–$C_6$ alkyl groups.

The above-mentioned free R' and R'' groups are suitably a lower alkyl group, preferably methyl.

The term "poly(alkylene oxide) group" means that said group comprises at least two alkyl ether groups successively connected to each other.

According to a preferred embodiment, the poly(alkylene oxide) groups are present in the elastomer in the form of poly(alkylene oxide) blocks having the formula $$—R^3—O(CHRCH_2O)_m R^4— \text{ or}$$
$$—CH_2CHR_1COO(CHRCH_2O)_m COCHR_1CH_2—$$

where R is hydrogen, a lower alkyl or phenyl, $R_1$ is hydrogen or a lower alkyl, $R^3$ and $R^4$ are the same or different and are straight chain or branched $C_2$–$C_6$ alkylene groups, and m is 1 to 30.

The elastomer composition suitably contains a filler, such as silica, in order that the membrane should obtain a sufficient strength.

The word "membrane" means the same as film.

General Description of the Method for the Preparation of the Elastomer Composition According to a preferred embodiment, the novel elastomer is prepared by crosslinking, in the presence of a catalyst, a vinyl-functional polymer component and a hydride-functional siloxane component in the absence of monomer. The present method does not employ monomer in the crosslinking reaction of the starting materials to form an elastomer. In this regard, the hydride-functional siloxane component of the present invention is not comparable to a monomer, since two hydride-functional siloxane components do not react with each other.

A remarkable advantage of the present inventive method over the prior art is that no toxic components are needed, since the crosslinking can be performed in the absence of monomers, in contrast to the prior art described above. The method according to this invention is furthermore a one-step process, thus more simple and more effective that the prior art methods.

By crosslinking is meant the addition reaction of the hydride-functional siloxane component with the carbon-carbon double bond of the vinyl-functional polymer component.

According to another embodiment, the elastomer is prepared by crosslinking the polymer in the presence of a peroxide catalyst, again in the absence of monomer. In this case the vinyl and methyl groups react with each other and form carbon-carbon bonds. A crosslink may also be formed between two methyl groups or between two vinyl groups.

For crosslinking, the amounts of the components are preferably selected so that the ratio of the molar amounts of the hydrides and the double bonds is at least 1.

The vinyl-functional polymer component may be
a) a vinyl-functional polysiloxane having the formula $$R'—SiR'R''O(SiR'R''O)_rSiR'R''R'$$

where R' and R'' are the same or different and are a lower alkyl group or a phenyl group, in which case said alkyl or phenyl group may be substituted or unsubstituted, and where some of the substituents R' and/or R'' have been substituted by vinyl groups, and r is 1 to 27000, or b) an alkenyl-terminated polysiloxane block copolymer having the formula $$T(AB)_xAT$$

where A is $—(SiR'R''O)_qSiR'R''—$, where R' and R'' are the same or different and are a lower alkyl group or a phenyl group, in which case said alkyl or phenyl group may be substituted or unsubstituted;
B is a poly(alkylene oxide) having the formula $$—R^3O(CHRCH_2O)_mR^4— \text{ or}$$
$$—CH_2CHR_1COO(CHRCH_2O)_mCOCHR_1CH_2—,$$

T is $R^1O(CHRCH_2O)_mR^3—$ or $CH_2=CR_1COO(CHRCH_2O)_mCOCHR_1CH_2—$ where R is hydrogen, a lower alkyl or phenyl, $R_1$ is hydrogen or a lower alkyl, $R^3$ and $R^4$ are the same or different and are straight-chain or branched $C_2$–$C_6$ alkylene groups, $R^1$ is a straight-chain or branched $C_2$–$C_6$ alkenyl group, m is 1 to 30, q is 1 to 3000, and x is 1 to 100, or c) a vinyl-functional polysiloxane copolymer having the formula $$R'—SiR'R''O(SiR'R''O)_r(SiR'R''O)_pSiR'R''—R'$$

where, in the first block, R' and R'' are the same or different and are a lower alkyl group, or a phenyl group, in which case said alkyl or phenyl group may be substituted or unsubstituted, and where some of the substituents R' and/or R'' have been substituted for by vinyl groups, and r is 1 to 27000, and where, in the second block, R' is a lower alkyl group, or an alkoxy-terminated poly(alkylene oxide) group having the formula $$R^3—O—(CHRCH_2O)_m\text{-alk}$$

where alk is a lower alkyl group, $R^3$ is a straight or branched $C_2$–$C_6$ alkylene group, R is hydrogen or a lower alkyl group, and m is 1 to 30, or R' is a phenyl group, in which case said alkyl or phenyl group may be substituted or unsubstituted, and R'' is a lower alkyl group or a phenyl group, in which case said alkyl or phenyl group may be substituted or unsubstituted, and p is 1 to 5000, or d) α,ω-dialkenyl poly(alkylene oxide) having the formula $$R^1—O—(CHRCH_2O)_m—R^2$$

where R is hydrogen or a lower alkyl, $R^1$ and $R^2$ are the same or different straight-chain or branched $C_2$–$C_6$ alkenyl groups, and m is 1 to 30, or e) a blend of a least two of the above-mentioned components a)–d).

If the formula of the vinyl-functional polysiloxane copolymer is, in accordance with the above description, $R'—SiR'R''O(SiR'R''O)_r(SiR'R''O)_pSiR'R''—R'$, it should be noted that the formula is a kind of gross formula, in which the blocks in successive parentheses may appear in any order in relation to one another. Furthermore, it is preferable that both a vinyl group and the above-mentioned alkoxy-terminated poly(alkylene oxide) group are not bonded to one and the same Si atom.

The hydride-functional siloxane component may be
a) a hydride-functional siloxane which may be straight chain, star shaped, branched or cyclic, or b) a hydride-terminated siloxane block copolymer having the formula $T(BA)_xBT$, where
T is $H—SiR'R''O(SiR'R''O)_qSiR'R''—$,
A is $—SiR'R''O(SiR'R''O)_qSiR'R''—$, where R' and R'' are the same or different and are a lower alkyl group or a phenyl group, in which case said alkyl or phenyl group may be substituted or unsubstituted;
B is a poly(alkylene oxide) having the formula $$—R^3—O—(CHRCH_2O)_m—R^4—, \text{ or}$$
$$—CH_2CHR_1COO(CHRCH_2O)_mCOCHR_1CH_2—$$

where R is hydrogen, a lower alkyl or phenyl, $R_1$ is hydrogen or a lower alkyl, $R^3$ and $R^4$ are the same or different and are straight-chain or branched $C_2$–$C_6$ alkylene groups, m is 1 to 30, q is 1 to 3000, and x is 0 to 100, or c) a blend of the above-mentioned components a) and b), provided that when the vinyl functional polymer component is a) a vinyl-functional polysiloxane or c) a vinyl-functional polysiloxane copolymer or a blend of a) and c) according to the above formulas, the hydride-functional siloxane component is b) a hydride-terminated siloxane block copolymer according to the above formula.

According to one embodiment, the hydride-functional siloxane copolymer may be straight-chain, in which case its formula is $$R'—SiR'R''O(SiR'R''O)_rSiR'R''R'$$

where R' and R'' are the same or different and are a lower alkyl group, or a phenyl in which case the said alkyl or phenyl group may substituted or unsubstituted, and where some of the substituents R' and/or R'' have been substituted for by hydrogen, and r is 1 to 27000.

The vinyl-functional polymer component may contain a filler, suitably silica.

The catalyst to be used in the crosslinking is suitably a noble metal catalyst, most commonly a platinum complex in alcohol, xylene, divinyl siloxane or cyclic vinyl siloxane. An especially suitable catalyst is a Pt(O)-divinyl tetramethyl disiloxane complex.

The elastomer composition made up of two elastomers is prepared so that initially a first elastomer is formed, whereafter a second elastomer is formed by crosslinking in the presence of the first elastomer. Thus the second elastomer will penetrate through the first elastomer.

The elastomer composition which comprises an elastomer and a straight-chain polymer is prepared, for example, by blending a vinyl-functional polymer component, a hydride-functional siloxane component, and a polymer which has no vinyl or hydride groups. In the crosslinking, the vinyl-functional polymer component and the hydride-functional siloxane component form an elastomer, but the polymer component which does not contain the said functional groups will not take part in the crosslinking reaction but will remain, in a straight-chain form, inside the elastomer.

The following table describes elastomer membranes of different composition types and their initial components.

TABLE 1

| Composition type | Polymers containing vinyl groups in the basic polymer blend | Crosslinking agent |
| --- | --- | --- |
| A | α,ω-divinyl ether poly(ethylene oxide)-poly(dimethyl siloxane) multi-block copolymer (PEO-(-PDMS-PEO)$_n$) | Hydride-functional siloxane |
| B | PEO-(PDMS-PEO)$_n$ and a siloxane polymer containing a filler | Hydride-functional siloxane |
| C | PEO-(PDMS-PEO)$_n$ together or separately with a siloxane polymer which does or does not contain a filler | α,ω-bis(dimethyl silyl hydride)-poly(dimethyl siloxane)-poly(ethylene oxide) multi-block copolymer (PDMS-PEO-PDMS)$_n$ together or separately with a hydride functional siloxane. |
| D | α,ω-divinyl ether poly(ethylene oxide) (PEODIVI) | Hydride-functional siloxane |
| E | PEODIVI and a siloxane polymer which does or does not contain a filler | Hydride-functional siloxane |
| F | PEO-grafted dimethyl siloxane-methyl vinyl siloxane copolymer (PDMS-PEO graft copolymer) | Hydride-functional siloxane |
| G | PDMS-PEO graft copolymer and a siloxane polymer which does or does not contain a filler | Hydride-functional siloxane |
| H | α,ω-diallyl ether poly(ethylene oxide)-(poly(dimethyl siloxane) multi-block copolymer (APEO-PDMS-APEO)$_n$) | Hydride-functional siloxane |
| I | PEO-(PDMS-PEO)$_n$ and a siloxane polymer which does or does not contain a filler | Peroxide |
| J | PDMS-PEO graft copolymer together or separately with a siloxane polymer which does or does not contain a filler | Peroxide |

EXAMPLE 1

Elastomer Membrane Prepared from Composition Type A

Ingredients used for the preparation of the elastomer membrane:

α,ω-divinyl ether PEO-PDMS block copolymer where the amount of PEO was 27.0% by weight and the vinyl content was 0.186 mmol/g.

Platinum catalyst Silopren U Katalysatoren Pt-D (Bayer AG), which had a platinum-siloxane complex in a vinyl-containing siloxane matrix. The platinum content was 1% by weight and the vinyl content was 0.5 mmol/g.

Crosslinking agent α,ω-di(trimethyl silyl)dimethyl siloxane-hydromethyl siloxane (DMS-HMS) copolymer Silopren U Vernetzer 730 (Bayer AG) having a Si—H content of 7.1 mmol/g, a molar mass of 2800 g/mol and a DMS group to HMS group ratio of 1:1.

Inhibitor 1-ethinyl-1-cyclohexanol (ETCH, Aldrich) having a decomposition temperature of +40° C.

The PEO(-PDMS-PEO)$_n$ which was used as the initial substance was prepared as follows:

50 g of anhydrous α,ω-divinyl ether poly(ethylene oxide) (PEODIVI) having a molar mass of 268 g/mol was weighed into a three-necked flask. In addition, 129.87 g of α,ω-bis (dimethyl silyl hydride) poly(dimethyl siloxane) (PDMSDIH, M$_n$=717 g/mol) and 30% by weight of toluene dried by distillation were weighed into the same vessel. Since vinyl groups were present in excess (3%) in the reaction, in the final product vinyl groups were obtained at both ends, which was essential for the subsequent crosslinking. The reaction solution was stirred over a magnetic stirring plate at 200 rpm, and dry oxygen was directed through the solution in order to prevent the deactivation of the catalyst. The reaction solution was heated to 50° C., whereafter the catalyst (Pt(O) divinyl-tetramethyl disiloxane complex) was added to the solution through the septum. The amount of platinum was 30 ppm, calculated from the amount of reactants. Thereafter the polymerization was monitored by means of IR until the reactions were complete (loss of the Si—H peak at 2130 cm$^{-1}$), which took approximately 4 h. After the polymerization, the toluene was distilled off from the solution by raising the temperature to 65° C. and by lowering the pressure to 5 mbar for a period of 1 h.

In the preparation of the elastomer, two blends were first prepared, portions I and II. Portion I contained PEO-(PDMS-PEO)$_n$, and the platinum catalyst. Portion II contained PEO-(PDMS-PEO)$_n$, the crosslinking agent and the inhibitor. Portions I and II were combined by mixing immediately before the crosslinking.

The amounts of the ingredients in the composition example in the final blend to be crosslinked were as follows:

Basic polymer PEO-(PDMS-PEO)$_n$ 94.87% by weight

Platinum catalyst 0.1% by weight

Crosslinking agent 5.00% by weight

Inhibitor 0.03% by weight

Portion I was prepared using a chamber mixer. 5.489 g of the basic polymer and 0.011 g of the platinum catalyst were weighed into the mixing chamber. The ingredients were agitated until the blend was homogeneous.

The crosslinking agent and the inhibitor were combined before being mixed with portion II. The mixture of the crosslinking agent and the inhibitor was prepared by weighing 0.059 g of ETCH and 9.941 g of Silopren U Vernetzer 730 into a glass vessel and by stirring the mixture in a water bath of +37° C. until ETCH had dissolved completely in the crosslinking agent. The amount of inhibitor in the mixture was 0.59% by weight.

Portion II was prepared using a chamber mixer. The mantle of the chamber mixer was cooled by water circulation to a point below room temperature, whereupon the temperature increase due to friction did not raise the temperature to the decomposition temperature of the inhibitor. 4.947 g of PEO-PDMS block copolymer and 0.553 g of the mixture of the crosslinking agent and the inhibitor were weighed into the mixing chamber. The ingredients were agitated until the blend was homogeneous.

Portions I and II were combined immediately before the crosslinking, by adding 5 grams of portion I and 5 grams of portion II into the mixing chamber of the chamber mixer. The ingredients were agitated until the blend was homogeneous. The blend was recovered and was drawn into vacuum to remove air bubbles. Four batches of 2 g of the blend were weighed and crosslinked successively in a hot-press.

The weighed blend was placed between two FEP release membranes in the center of a round metal form having a thickness of 0.4 mm and an inner diameter of 8 cm. The blend, together with the forms and the FEP membranes, was placed between the compression surfaces of the hot-press, which surfaces had been heated in advance to +115° C. The surfaces were pressed together and were kept pressed at a pressure of 200 bar for 5 minutes. The pressure was released and the membrane was allowed to set at room temperature for 24 hours. Round test pieces having a diameter of 22 mm were cut out from the membranes by means of a puncher.

EXAMPLE 2

Elastomer Membrane Prepared from Composition Type B

Ingredients used for the preparation of the elastomer membrane:

The PEO(-PDMS-PEO)$_n$ was the same as in Example 1, except that the amount of PEO had been increased to 28.0% by weight and the vinyl content to 0.24 mmol/g by increasing the proportion of PEODIVI in the synthesis of the block copolymer.

The catalyst, the cross linking agent and the inhibitor were the same as in Example 1.

The siloxane polymer which contained filler was a dimethyl siloxane-vinyl methyl siloxane (DMS-VMS) copolymer containing a silica filler and having a molar mass of $M_n$=400,000 g/mol. The vinyl content of the blend was 0.011 mmol/g. There was 36% by weight of silica mixed in the polymer, and the silica was surface-treated with α,ω-bis(dimethyl hydroxysilyl)poly(dimethyl siloxane) (M=520 g/mol), which was present in an amount of 12% by weight in the blend.

The amounts of ingredients in the composition example were as follows:

PEO(-PDMS-PEO)$_n$ 32.8% by weight

DMS-VMS copolymer containing a silica filler, 60.9% by weight

Platinum catalyst 0.1% by weight

Crosslinking agent 6.19% by weight

Inhibitor 0.03% by weight

First the basic polymer blend was prepared in a chamber mixer. 4.2 grams of the PEO(-PDMS-PEO)$_n$ block copolymer and 7.8 grams of the DMS-VMS copolymer containing a silica filler were weighed into the mixing chamber. The ingredients were agitated until the blend was homogeneous.

Portion I was Prepared as in Example 1.

The combining of the crosslinking agent and the inhibitor was done, as in Example 1, before mixing with portion II, except that ETCH was weighed in an amount of 0.048 g and Silopren U Vernetzer 730 in an amount of 9.952 g. The amount of inhibitor in the blend was 0.48% by weight.

Portion II was prepared as in Example 1, except that the basic polymer blend was weighed in an amount of 4.816 grams and the mixture of the crosslinking agent and the inhibitor in an amount of 0.684 grams.

Portions I and II were combined as in Example 1. Four batches of 2.1 g of the blend were weighed and were crosslinked successively in a hot-press, as in Example 1.

EXAMPLE 3

Elastomer Membrane Prepared from Composition Type C

Ingredients used for the preparation of the elastomer membrane:

The PEO(-PDMS-PEO)$_n$ was the same as in Example 2. The catalyst and the inhibitor were the same as in Examples 1 and 2.

The dimethyl siloxane-vinyl methyl siloxane (DMS-VMS) copolymer containing a silica filler was the same as in Example 2.

The crosslinking agent used was a PDMS-(-PEO-PDMS)$_n$ copolymer having a Si—H content of 0.26 mmol/g, and the amount of PEO in it was 23.6% by weight.

The said crosslinking agent was prepared as follows:

40 g of an anhydrous α,ω-divinyl ether poly(ethylene oxide)(PEODIVI) having a molar mass of 246.3 g/mol was weighed into a three-necked flask. In addition, 129.4 g of α,ω-bis(dimethyl silyl hydride)poly(dimethyl siloxane) (PDMSDIH, $M_n$=717 g/mol) and 30% by weight of toluene dried by distillation were weighed into the same vessel. Since dimethyl silyl hydride groups were present in excess (10%) in the reaction, dimethyl silyl hydride groups were obtained at both ends in the final product. The reaction solution was stirred over a magnetic stirring plate at 200 rpm, and dry oxygen was directed through the solution to prevent the deactivation of the catalyst. The reaction solution was heated to 50° C., whereafter the catalyst (Pt(O) divinyl-tetramethyl siloxane complex) was added to the solution through the septum. The amount of platinum was 30 ppm, calculated from the amount of the reactants. Thereafter the polymerization was monitored by means of IR until the reactions were complete (loss of the vinyl peak at 1600 cm$^{-1}$), which took approximately 4 h. After the polymerization, the toluene was removed from the solution by distillation by raising the temperature to 65° C. and by lowering the pressure to 5 mbar for a period of 1 h.

The amounts of the ingredients in the composition example were as follows:

PEO(-PDMS-PEO)$_n$ 1.10% by weight

DMS-VMS containing a silica filler, 85.50% by weight

Platinum catalyst 0.10% by weight

Crosslinking agent α,ω-bis-(dimethyl silyl hydride) PEO-PDMS 13.27% by weight

Inhibitor 0.03% by weight

First the basic polymer blend was prepared in a chamber mixer. 0.15 grams of the α,ω-divinyl ether PEO-PDMS block copolymer and 11.85 grams of the DMS-VMS copolymer containing a silica filler were weighed into the mixing chamber. The ingredients were agitated until the blend was homogeneous.

Portion I was prepared as in Example 1. The combining of the crosslinking agent and the inhibitor was done, as in Example 1, before mixing with portion II, except that ETCH was weighed in an amount of 0.022 g and PDMS-(PEO-PDMS)$_n$ block copolymer in an amount of 9.978 g instead of Vernetzer 730. The amount of inhibitor in the blend was 0.22% by weight.

Portion II was prepared as in Example 1, except that the basic polymer blend was weighed in an amount of 4.04 grams and the mixture of the crosslinking agent and the inhibitor in an amount of 1.46 grams.

Portions I and II were combined as in Example 1. Four batches of 2.1 g of the blend were weighed and were successively crosslinked in a hot-press, as in Example 1.

EXAMPLE 4

Elastomer Membrane Prepared from Composition Type D

Ingredients used for the preparation of the elastomer membrane:

α,ω-divinyl ether poly(ethylene oxide) (PEODIVI) (polyethylene glycol divinyl ether, Aldrich, $M_n$=240 g/mol). The vinyl amount obtained by titration was 7.4 mmol/g.

Catalyst Gelest SIP 6831.0, platinum-siloxane complex in xylene, platinum content 2.25% by weight.

The crosslinking agent and the inhibitor were the same as in Example 1.

The amounts of the ingredients in the composition example were as follows:

PEODIVI 52.231% by weight

Platinum catalyst 0.045% by weight

Crosslinking agent 47.694% by weight

Inhibitor 0.030% by weight

First a mixture of the crosslinking agent and the inhibitor was prepared as in Example 1, except that the inhibitor was weighed in an amount of 0.0063 grams and the crosslinking agent in an amount of 9.9937 grams. The amount of inhibitor in the mixture was 0.063% by weight.

5.2231 grams of PEODIVI and 0.0045 grams of the platinum catalyst were mixed together in a glass vessel. 4.772 grams of the mixture of the crosslinking agent and the inhibitor was mixed into it.

Eight batches of 0.8 g of the blend were weighed into flat-bottomed aluminum forms having a diameter of 5 cm and having a FEP membrane on the bottom. The forms were placed under a 100 mbar vacuum at +115° C. for a period of 15 minutes. Test pieces were cut out from the elastomer obtained.

EXAMPLE 5

Elastomer Membrane Prepared from Composition Type E

Ingredients used for the preparation of the elastomer membrane:

PEODIVI, the same as in Example 4.

DMS-VMS copolymer, the same as in Example 2.

The catalyst, the crosslinking agent and the inhibitor were the same as in Example 1.

The amounts of the ingredients in the composition example were as follows:

PEODIVI 11.37% by weight

DMS-VMS copolymer 64.46% by weight

Platinum catalyst 0.1% by weight

Crosslinking agent 24.03% by weight

Inhibitor 0.03% by weight

First, a mixture of the crosslinking agent and the inhibitor was prepared, as in Example 1, except that the inhibitor was weighed in an amount of 0.0125 grams and the crosslinking agent in an amount of 9.9875 grams. The amount of inhibitor in the mixture was 0.125% by weight.

1.138 grams of PEODIVI and 6.446 grams of DMS-VMS copolymer were mixed together in a chamber mixer. 0.01 grams of platinum catalyst was added, and the blend was agitated until homogeneous. 2.406 grams of the mixture of the crosslinking agent and the inhibitor was added and the blend was agitated until homogeneous.

Four batches of 2.1 g of the blend were weighed and were successively crosslinked in a hot-press, as in Example 1.

EXAMPLE 6

Elastomer Membrane Prepared from Composition Type F

Ingredients used for the preparation of the elastomer membrane:

PDMS-PEO graft copolymer having a vinyl concentration of 0.0743 mmol/g and a PEO content of 1.28% by weight.

The catalyst, the crosslinking agent and the inhibitor were the same as in composition A.

The PDMS-PEO graft copolymer used was prepared as follows:

600 g of octamethyl cyclotetrasiloxane ($D_4$), 9.28 g of poly-(dimethyl siloxane)-poly(ethylene oxide) graft copolymer (Gelest, DBE-821, containing 80% by weight PEO), 6.18 g of dimethyl vinyl silyl end-blocked PDMS (end-blocker, Bayer Silopren U2), and 3.1 g of tetramethyl tetravinyl cyclotetrasiloxane were weighed. The reactor was nitrogenated, the weighed chemicals were poured in, and stirring was started. The inside temperature of the reactor was raised to 135° C., and the catalyst (potassium siloxanolate, 0.9 ml, 20 ppm K+) was added to the reaction solution. The viscosity of the reaction solution began to increase vigorously, and at 1 h from the adding of the catalyst it was possible to deactivate the catalyst by increasing the reactor pressure to 2 bar for a period of 15 minutes by means of carbon dioxide. Thereafter the light cyclic compounds (13% by weight) were removed from the reaction solution by distillation (10 mbar, 30 min, 135° C.) Product $M_n$=190,000 g/mol.

The amounts of the ingredients in the composition example were as follows:

Basic polymer PDMS-PEO graft copolymer 96.10% by weight

Platinum catalyst 0.5% by weight

Crosslinking agent 3.06% by weight

Inhibitor 0.34% by weight

The combining of the crosslinking agent and the inhibitor was done as in Example 1, except that ETCH was weighed in an amount of 1.0 g and Silopren U Vernetzer 730 in an amount of 9.0 g. The amount of inhibitor in the mixture was 10% by weight.

9.61 grams of the PDMS-PEO graft copolymer and 0.05 grams of the platinum catalyst were mixed together. 0.34 grams of the mixture of the crosslinking agent and the inhibitor was added and the blend was stirred until homogeneous.

Four batches of 2.1 g of the blend were weighed and were successively crosslinked in a hot-press, as in Example 1.

EXAMPLE 7

Elastomer Membrane Prepared from Composition Type G

Ingredients used for the preparation of the elastomer membrane:

The PDMS-PEO graft copolymer was the same as in Example 6.

The DMS-VMS copolymer was the same as in Example 2.

The catalyst, the crosslinking agent and the inhibitor were the same as in Example 1.

The amounts of the ingredients in the composition example were as follows:

PDMS-PEO graft copolymer 26.75% by weight

DMS-VMS copolymer 72.31% by weight

Platinum catalyst 0.10% by weight

Crosslinking agent 0.81% by weight

Inhibitor 0.03% by weight

The combining of the crosslinking agent and the inhibitor was done as in Example 1, except that ETCH was weighed in an amount of 0.36 g and Silopren U Vernetzer 730 in an amount of 9.64 g. The amount of inhibitor in the mixture was 3.6% by weight.

2.675 grams of the PDMS-PEO graft copolymer and 7.231 grams of the DMS-VMS copolymer containing a filler were mixed together. 0.01 grams of the platinum catalyst was added and the blend was stirred until homogeneous. 0.084 grams of the mixture of the crosslinking agent and the inhibitor was added and the blend was stirred until homogeneous.

Four batches of 2.1 g of the blend were weighed and were successively crosslinked in a hot-press, as in Example 1.

EXAMPLE 8

Elastomer Membrane Prepared from Composition Type H

Ingredients used for the preparation of the elastomer membrane:

APEO-(-PDMS-APEO)$_n$, where the amount of PEO was 10.3% byweight and the vinyl content 0.063 mmol/g.

The catalyst was the same as in Example 4.

The inhibitor was the same as in Example 1.

The crosslinking agent was a DMS-HMS copolymer which contained 22.5% by weight methyl hydride siloxane groups (Gelest).

The APEO-(-PDMS-APEO)$_n$ used was prepared as follows:

Anhydrous α,ω-diallyl poly(ethylene oxide) (PEODIAL) which had a molar mass of 520 g/mol and which was prepared by adapting the procedure disclosed in the publication Mei Hui, Yang, Laing-Jong, Li, and Tsang-Feng, Ho, Synthesis and Characterization of polymethylsiloxane/poly(ethylene glycol) monomethyl ether copolymers, J. Ch. Colloid & Interface Soc. 3(17), 1994, 19–28 and α,ω-bis(dimethyl silyl hydride) poly(dimethyl siloxane) (PDMSDIH, M$_n$=6000 g/mol) were weighed into a three-necked flask. The mass of the PEODIAL was 1.38 g (M$_n$=520 g/mol, 5.28 mmol of allyl groups) and the mass of PDMSDIH was 12 g (4.8 mmol of hydride groups), the amount of allyl groups being 10% greater than that of hydride groups. Thus an α,ω-diallyl-end-blocked final product was ensured.

In addition, toluene was weighed into the reaction vessel in an amount of 45% by weight (7.2 g). The reaction mixture was stirred over a magnetic stirring plate at 200 rpm, and dry oxygen was bubbled through the mixture in order to prevent the deactivation of the catalyst. The temperature of the reaction mixture was raised to 60° C. Thereafter the catalyst (Pt(O) divinyl tetramethyl disiloxane complex) was added to the reaction solution through the septum, cautiously one drop at the time. The amount of platinum was 50 ppm, calculated from the reactants. The polymerization was allowed to proceed for approximately 6 h, whereafter the completion of the polymerization was confirmed by IR (loss of the Si—H peak at 2130 cm$^{-1}$). For the removal of the toluene by distillation, the temperature was raised to 65° C. and the pressure was lowered to 5 mbar for a period of 30 min.

The amounts of the ingredients of the composition example were as follows:

APEO-(-PMDS-APEO)$_n$ 94.68% by weight

Platinum catalyst 0.5% by weight

Crosslinking agent 4.7% by weight

Inhibitor 0.12% by weight 3.0 grams of the APEO-(-PMDS-APEO)$_n$, 0.0158 grams of the and 0.0038 g of the inhibitor, and 0.1490 g of the crosslinking agent were mixed together. The air bubbles were removed from the mixture, and the mixture was crosslinked in a hot-press at 110° C. for 15 minutes and was cured at 110° C. for 15 minutes.

EXAMPLE 9

Elastomer Membrane Prepared from Composition Type I

Ingredients used for the elastomer membrane:

PEO-(PDMS-PEO)$_n$, where the amount of PEO was 5.0% by weight and the vinyl content was 0.04 mmol/g.

The DMS-VMS copolymer containing a silica filler was the same as in Example 2.

Dichlorobenzoyl peroxide (Perkadox PD50 S, Nusil).

The PEO-(PDMS-PEO)$_n$ used was prepared as follows: 0.528 g of anhydrous α,ω-divinyl ether polyethylene oxide) (PEODIVI) having a molar mass of 240 g/mol was weighed into a three-necked flask. 10 g of α,ω-bis(dimethyl silyl hydride) poly(dimethyl silyl siloxane) (PDMSDIH) having a molar mass of 6000 g/mol was weighed into the same vessel. The PDMSDIH contained hydride groups in an amount of 0.04% by weight, and thus the amount of hydride groups in 10 grams was 4 mmol and the amount of PEODIVI vinyl groups was 4.4 mmol. Since the vinyl groups were present in excess (10%) in the reaction, vinyl groups were obtained at both ends of the final product, a fact essential for the subsequent crosslinking. In addition, to facilitate and to prevent the reaction from occurring too vigorously, toluene dried by distillation was added to the reaction mixture so that the proportion of toluene was 30% by weight (4.5 g). The reaction solution was stirred over a magnetic stirring plate at 200 rpm, and dry oxygen was directed through the solution; this prevented the catalyst from converting to metallic form and thus prevented the deactivation of the catalyst. The reaction solution was heated to 50° C., whereafter the catalyst (Pt(O) divinyl tetramethyl disiloxane complex) was added to the mixture through the septum. The amount of platinum was 50 ppm, calculated from the amount of the reactants. The catalyst was added dropwise, whereby hot spots in the reactor were avoided. After the adding of the catalyst the reaction was allowed to proceed for 2 h. Thereafter the completion of the reaction was confirmed by IR (loss of the Si—H peak at 2130 cm$^{-1}$). After the polymerization the reaction mixture was heated to 65° C. and the toluene was removed by vacuum distillation (5 mbar) in the course of 30 minutes.

The amounts of ingredients in the composition example were as follows:

PEO-(PDMS-PEO)$_n$, 4.9% by weight silica-filled DMS-VMS copolymer, 93.9% by weight dichlorobenzoyl peroxide (Perkadox PD50 S, Nusil), 1.2% by weight.

0.5 g of PEO-(PDMS-PEO)$_n$ and 9.5 g of a DMS-VMS copolymer containing a filler were mixed together. 0.12 g of the peroxide catalyst was mixed with the homogeneous blend, and the blend was hardened at a temperature of +115° C. and a pressure of 200 bar for 5 minutes and was cured at +150° C. for 2 hours.

EXAMPLE 10

Elastomer Membrane Prepared from Composition Type J

Ingredients used for the preparation of the elastomer:

PDMS-PEO graft copolymer the same as in Example 6

Dichlorobenzoyl peroxide Perkadox PD50 S, Nusil

The amounts of the ingredients in the composition example were as follows:

PDMS-PEO graft copolymer 98.8% by weight

Dichlorobenzoyl peroxide Perkadox PD50 S 1.2% by weight 10 grams of the PDMS-PEO graft copolymer and 0.12 grams of Perkadox PD50 S were mixed together. The blend was hardened at a temperature of +115° C. and a pressure of 200 bar for 5 minutes and was cured at +150° C. for 2 hours.

The applicants have measured the glass transition temperatures of the elastomer compositions according to the present invention by differential scanning calorimetry (DSC). For example, for a block copolymer of PEO and PDMS that has been prepared by crosslinking triethyleneglycol divinylether having three PEO-groups and hydride-terminated polydimethylsiloxane having ten repeating units, the glass transition temperature, measured in nitrogen, was −104° C. All elastomer compositions tested had a glass transition temperature below −100° C.

Permeation Tests

Various compositions, in which the amount of PEO groups varied, were prepared of the above-mentioned composition types A–J. Composition types A–G were tested for the permeation rates of various drugs.

The assay apparatus described in the publication Yie W. Chien, Transdermal Controlled Systemic Medications, Marcel Dekker Inc., New York and Basel 1987, page 173, was used in the tests.

The drug fluxes (permeations) through membranes were measured with a two-compartment diffusion cell at 37° C. (side-by-side diffusion cell, Crown Glass Company). The apparatus consisted of two concentric cells (donor and receptor compartments) that were separated by the elastomer membrane to be investigated. The donor and receptor compartments were both jacketed and thermostated by an external circulating bath and each compartment had a magnetic stirrer. A drug solution and solvent (without drug) was added into the donor and the receptor compartments. At each predetermined time interval, samples were withdrawn from the receptor compartment and replaced with the same volume of solvent. The amount of the drug that permeated through the membrane was measured by HPLC. In all measurements, the thickness (0.4 mm) of the membrane and the surface area of the membranes were constant.

In the tests described below, the permeation rates of two different drugs through a 0.4-mm-thick elastomer membrane were measured by using the assay apparatus described above. The tables below show the effect of the concentration of PEO groups (% by weight of the said compositions) on the permeation rates of the different drugs for elastomers prepared from different composition types. The tables show the relative permeation as compared with a commercial crosslinked dimethyl siloxane-vinyl methyl siloxane elastomer ($M_n$ approximately 400,000 g/mol) containing a silica filler.

| Composition type | PEO concentration % by weight | Relative permeation |
|---|---|---|
| Drug 1: Levonorgestrel | | |
| comparison | 0 | 1 |
| A | 28.8 | 14.5 |
| B | 3.8 | 1.5 |
| B | 4.1 | 2.0 |
| B | 5.0 | 2.3 |
| Drug 2: 17-β-Estradiol | | |
| comparison | 0 | 1 |
| A | 11.6 | 21.3 |
| A | 26.4 | 110 |
| B | 7.8 | 13.3 |
| B | 9.8 | 24.4 |
| C | 3.4 | 4.6 |
| D | 52.3 | 90.4 |
| E | 11.4 | 7.7 |
| F | 1.3 | 2.4 |
| G | 0.5 | 1.4 |

The permeation tests performed showed that an increasing concentration of PEO in the membrane increased the permeation rate for each composition type and for each drug tested, regardless of whether the drug concerned was hydrophilic or lipophilic.

An elastomer composition according to the invention is, for example, highly suited for controlling, in implants and in intrauterine and intravaginal devices, the permeation rates of drugs having hormonal action.

The most important drugs having hormonal action include antiprogestins, progestins, estradiols and androgens.

The above embodiments of the invention are only examples of the implementation of the idea of the invention. For a person skilled in the art it is clear that the different embodiments of the invention may vary within the framework of the claims presented below.

We claim:

1. A membrane or matrix for controlling the permeation rate of a drug, the membrane or matrix comprising a siloxane elastomer composition comprising at least one elastomer and optionally a non-crosslinked polymer, wherein the elastomer composition comprises poly(alkylene oxide) groups and said poly(alkylene oxide) groups are present as blocks in a chain of said elastomer or non-crosslinked polymer, or as blocks and alkoxy-terminated grafts of polysiloxane groups, said blocks or blocks and grafts being linked to the polysiloxane groups in said chain by silicon-carbon bonds, and said elastomer composition is amorphous below its glass transition temperature of less than 35° C., wherein the formula of the polysiloxane groups is —(SiR'R"O)$_q$SiR'R"— where R' and R" are selected from the group consisting of a) groups which are the same or different and which are a lower alkyl group or a phenyl group in which case said alkyl or phenyl group may be substituted or unsubstituted, or alkoxy-terminated poly(alkylene oxide) groups having the formula —R$^3$—O—(CHRCH$_2$O)$_m$-alk, where alk is a lower alkyl group, R is hydrogen or lower alkyl, R$^3$ is a linear or branched C$_2$–C$_6$ alkylene and m is 1 to 30, b) bonds formed from the hydrogen or alkenyl groups to other polymer chains in the elastomer, and as alkoxy-terminated grafts of polysiloxane groups or as blocks or as a mixture of said grafts and said blocks, the said grafts or blocks being linked to the polysiloxane groups by silicon-carbon bonds, c) optionally unreacted groups selected from the group consisting of hydrogen, vinyl and vinyl-terminated alkene, and q is 1 to 3000;

and wherein said poly(alkylene oxide) groups have the following formula:

—R$^3$—O (CHRCH$_2$O)$_m$R$^4$—.

where R is hydrogen, a lower alkyl or phenyl, R$_1$ is hydrogen or a lower alkyl, R$^3$ and R$^4$ are the same or different and are straight chain or branched C$_2$–C$_6$ alkylene groups, and m is 1 to 30, with the proviso that there must be at least three poly(alkylene oxide) blocks present in said chain of said siloxane elastomer.

2. The membrane or matrix of claim 1, wherein the poly(alkylene oxide) groups are present in said elastomer composition as blocks.

3. The membrane or matrix of claim 1, wherein said poly(alkylene oxide) groups are poly(ethylene oxide) groups.

4. The membrane or matrix of claim 1, wherein R' and R" groups are free groups, and said free groups are lower alkyl groups.

5. The membrane or matrix of claim 1, wherein the elastomer composition is made up of two elastomers interlaced one inside the other, wherein the first elastomer comprises poly(alkylene oxide) groups and the poly(alkylene oxide) groups are present in the elastomer as blocks, or as blocks and alkoxy-terminated grafts of polysiloxane groups, the said blocks or blocks and grafts being linked to the polysiloxane groups by silicon-carbon bonds, or as a mixture of these forms, and wherein the second elastomer comprises a siloxane elastomer.

6. The membrane or matrix of claim 5, wherein the second elastomer is a poly(dimethyl siloxane) elastomer which optionally includes poly(alkylene oxide) groups.

7. The membrane or matrix of claim 6, wherein the optional poly(alkylene oxide) groups of said second elastomer are present in the form of blocks, or as blocks and alkoxy-terminated grafts of polysiloxane groups, said blocks or blocks and grafts being linked to the polysiloxane groups by silicon-carbon bonds.

8. The membrane or matrix of claim 1, wherein the elastomer composition is a blend which comprises a siloxane elastomer and a straight-chain polysiloxane copolymer which comprises poly(alkylene oxide) groups, wherein the poly(alkylene oxide) groups are present in said polymer as blocks, or as blocks and alkoxy-terminated grafts of polysiloxane groups, said blocks or blocks and grafts being linked to the polysiloxane groups by silicon-carbon bonds.

9. The membrane or matrix of claim 8, wherein the poly(alkylene oxide) groups are poly(ethylene oxide) groups.

10. The membrane or matrix of claim 8, wherein the formula of the polysiloxane groups is

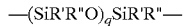
—(SiR'R"O)$_q$SiR'R"— where R' and R" are the same or different and which are a lower alkyl group or a phenyl group, in which case said alkyl or phenyl group may be substituted or unsubstituted, or alkoxy-terminated poly(alkylene oxide) groups having the formula —R$^3$—O—(CHRCH$_2$O)$_m$alk, where alk is a lower alkyl group, R is hydrogen or lower alkyl, R$^3$ is a linear or branched C$_2$–C$_6$ alkylene group and m is 1 to 30, and q is 1 to 3000.

11. The membrane or matrix of claim 10, wherein R'0 and R" groups are free groups, and said free R' and R" groups are lower alkyl groups.

12. The membrane or matrix of claim 8, wherein the poly(alkylene oxide) groups are present in the straight-chain polysiloxane polymer in the form of poly(alkylene oxide) blocks having the formula

—R$^3$—O(CHRCH$_2$O)$_m$R$^4$— or
—CH$_2$CHR$_1$COO(CHRCH$_2$O)$_m$COCHR$_1$CH$_2$— where R is hydrogen, a lower alkyl or phenyl, R$_1$ is hydrogen or a lower alkyl, R$^3$ and R$^4$ are the same or different and are straight chain or branched C$_2$–C$_6$ alkylene groups, and m is 1 to 30.

13. The membrane or matrix of claim 8, wherein the siloxane elastomer comprises poly(dimethyl siloxane).

14. The membrane or matrix of claim 8, wherein the siloxane elastomer comprises poly(alkylene oxide) groups, and wherein poly(alkylene oxide) groups are present in the elastomer as blocks, or as blocks and alkoxy-terminated grafts of polysiloxane groups, said blocks or blocks and grafts being linked to the polysiloxane groups by silicon-carbon bonds.

15. The membrane or matrix of claim 1, further comprising a filler.

16. A method for the preparation of a siloxane elastomer, comprising
a) crosslinking a vinyl-functional polymer component and a hydride-functional component in the presence of a catalyst and in the absence of monomer, or
b) crosslinking a polymer component in the presence of a peroxide catalyst and in the absence of monomer,
wherein (alkylene oxide) groups are present in the elastomer or polymer as blocks in a chain of said elastomer or polymer, or as blocks and alkoxy-terminated grafts of polysiloxane groups, said blocks or blocks and grafts being linked to polysiloxane groups in said chain by silicon-carbon bonds, there being at least three blocks in said chain of said elastomer composition,
wherein the formula of the polysiloxane groups is

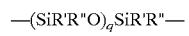
—(SiR'R"O)$_q$SiR'R"— where R' and R" are selected from the group consisting of
a) groups which are the same or different and which are a lower alkyl group or a phenyl group in which case said alkyl or phenyl group may be substituted or unsubstituted, or alkoxy-terminated poly(alkylene oxide) groups having the formula —R$^3$—O—(CHRCH$_2$O)$_m$—-alk, where alk is a lower alkyl group, R is hydrogen or lower alkyl, R$^3$ is a linear or branched C$_2$–C$_6$ alkylene and m is 1 to 30,
b) bonds formed from the hydrogen or alkenyl groups to other polymer chains in the elastomer, and as alkoxy-terminated grafts of polysiloxane groups or as blocks or as a mixture of said grafts and said blocks, the said grafts or blocks being linked to the polysiloxane groups by silicon-carbon bonds,
c) optionally unreacted groups selected from the group consisting of hydrogen, vinyl and vinyl-terminated alkene, and q is 1 to 3000;
and wherein said poly(alkylene oxide) groups have the following formula:

—R$^3$—O(CHRCH$_2$O)$_m$R$^4$— where R is hydrogen, a lower alkyl or phenyl, R$_1$ is hydrogen or a lower alkyl, R$^3$ and R$^4$ are the same or different and are straight chain or branched C$_2$–C$_6$ alkylene groups, and m is 1 to 30.

17. The method of claim 16, wherein the amounts of the vinyl-functional component and the hydride-functional component are selected so that the ratio of the molar amount of hydrides to the molar amount of the double bonds is at least 1.

18. The method of claim 16, wherein
I) the vinyl-functional polymer component is
a) a vinyl-functional polysiloxane having the formula

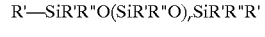
R'—SiR'R"O(SiR'R"O)$_r$SiR'R"R' where R' and R" are the same or different and are a lower alkyl group or a phenyl group, in which case said alkyl or phenyl group may be substituted or unsubstituted, and where some of the substituents R' and/or R" have been substituted by vinyl groups, and r is 1 to 27000, or b) an alkenyl-terminated polysiloxane block copolymer having the formula $$T(AB)_xAT$$

where A is $-(SiR'R''O)_qSiR'R''-$, where R' and R'' are the same or different and are a lower alkyl group or a phenyl group, in which case said alkyl or phenyl group may be substituted or unsubstituted;

B is a poly(alkylene oxide) having the formula $$-R^3O(CHRCH_2O)_mR^4-$$

T is $R^1O(CHRCH_2O)_mR^3-$ where R is hydrogen, a lower alkyl or phenyl, $R_1$ is hydrogen or a lower alkyl, $R^3$ and $R^4$ are the same or different and are straight-chain or branched $C_2-C_6$ alkylene groups, $R^1$ is a straight-chain or branched $C_2-C_6$ alkenyl group, m is 1 to 30, q is 1 to 3000, and x is 1 to 100, or c) a vinyl-functional polysiloxane copolymer having the formula $$R'-SiR'R''O(SiR'R''O)_r(SiR'R''O)_pSiR'R''-R'$$

where, in the first block, R' and R'' are the same or different and are a lower alkyl group, or a phenyl group, in which case said alkyl or phenyl group may be substituted or unsubstituted, and where some of the substituents R' and/or R'' have been substituted for by vinyl groups, and r is 1 to 27000, and where, in the second block, R' is a lower alkyl group, or an alkoxy-terminated poly(alkylene oxide) group having the formula $$R^3-O-(CHRCH_2O)_m alk$$

where alk is a lower alkyl group, $R^3$ is a straight or branched $C_2-C_6$ alkylene group, R is hydrogen or a lower alkyl group, and m is 1 to 30, or R' is a phenyl group, in which case said alkyl or phenyl group may be substituted or unsubstituted, and R'' is a lower alkyl group or a phenyl group, in which case said alkyl or phenyl group may be substituted or unsubstituted, and p is 1 to 5000, or d) α,ω-dialkenyl poly(alkylene oxide) having the formula $$R^1-O-(CHRCH_2O)_m-R^2$$

where R is hydrogen or a lower alkyl, $R^1$ and $R^2$ are the same or different straight-chain or branched $C_2-C_6$ alkenyl groups, and m is 1 to 30, or e) a blend of a least two of the above-mentioned components a)–d) and II) the hydride-functional component is
   a) a hydride-functional siloxane which may be straight chain, star shaped, branched or cyclic, or
   b) a hydride-terminated siloxane block copolymer having the formula $T(BA)_xBT$, where T is $H-SiR'R''O(SiR'R''O)_qSiR'R''-$, A is $-SiR'R''O(SiR'R''O)_qSiR'R''-$, where R' and R'' are the same or different and are a lower alkyl group or a phenyl group, in which case said alkyl or phenyl group may be substituted or unsubstituted;

B is a poly(alkylene oxide) having the formula $$R^3-O-(CHRCH_2O)_m-R^4-,$$

where R is hydrogen, a lower alkyl or phenyl, $R_1$ is hydrogen or a lower alkyl, $R^3$ and $R^4$ are the same or different and are straight-chain or branched $C_2-C_6$ alkylene groups, m is 1 to 30, q is 1 to 3000, and x is 0 to 100, or c) a blend of the above-mentioned components a) and b), provided that when the vinyl functional polymer component is a) a vinyl-functional polysiloxane or c) a vinyl-functional polysiloxane copolymer or a blend of a) and c) according to the above formulas, the hydride-functional siloxane component is b) a hydride-terminated siloxane block copolymer according to the above formula.

19. The method of claim 18, wherein the hydride-functional siloxane copolymer is straight-chain, and that its formula is $$R'-SiR'R''O(SiR'R''O)_rSiR'R''R',$$

where R' and R'' are the same or different and are a lower alkyl group or a phenyl group, in which case said alkyl or phenyl group may be substituted or unsubstituted, and where some of the substituents R' and/or R'' have been substituted for by hydrogen, and r is 1 to 27000.

20. The method of claim 16, wherein the vinyl-functional polymer component contains a filler.

* * * * *